United States Patent
Gerdts et al.

(10) Patent No.: US 10,695,202 B2
(45) Date of Patent: *Jun. 30, 2020

(54) MEDICAL SYSTEMS AND RELATED METHOD

(71) Applicant: Boston Scientific Scimed, Inc., Maple Grove, MN (US)

(72) Inventors: Michael D. Gerdts, Big Lake, MN (US); John R. Moberg, Elk River, MN (US); James J. Ford, West St. Paul, MN (US); Theresa Ditter, Shoreview, MN (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 117 days.

This patent is subject to a terminal disclaimer.

(21) Appl. No.: 15/654,010

(22) Filed: Jul. 19, 2017

(65) Prior Publication Data

US 2017/0312107 A1 Nov. 2, 2017

Related U.S. Application Data

(63) Continuation of application No. 14/300,334, filed on Jun. 10, 2014, now Pat. No. 9,717,613, which is a continuation of application No. 12/022,513, filed on Jan. 30, 2008, now Pat. No. 8,758,421.

(51) Int. Cl.
*A61F 2/95* (2013.01)
*A61F 2/966* (2013.01)
*A61F 2/06* (2013.01)

(52) U.S. Cl.
CPC ............... *A61F 2/95* (2013.01); *A61F 2/966* (2013.01); *A61F 2002/9517* (2013.01); *A61F 2250/0029* (2013.01)

(58) Field of Classification Search
CPC .... A61F 2/95; A61F 2/962; A61F 2002/9505; A61F 2002/9528; A61F 2002/9534; A61F 2002/9517
See application file for complete search history.

(56) References Cited

U.S. PATENT DOCUMENTS

| | | |
|---|---|---|
| 4,655,771 A | 4/1987 | Wallsten |
| 4,848,343 A | 7/1989 | Wallsten et al. |
| 4,990,151 A | 2/1991 | Wallsten |
| 5,026,377 A | 6/1991 | Burton et al. |
| 5,324,269 A | 6/1994 | Miraki |
| 5,360,401 A | 11/1994 | Turnland |
| 5,389,087 A | 2/1995 | Miraki |

(Continued)

FOREIGN PATENT DOCUMENTS

| | | |
|---|---|---|
| EP | 050686 B1 | 9/1992 |
| EP | 1095634 B1 | 5/2007 |

(Continued)

*Primary Examiner* — Tuan V Nguyen
(74) *Attorney, Agent, or Firm* — Seager, Tufte & Wickhem, LLP

(57) ABSTRACT

Medical systems and related methods are disclosed. In some embodiments, the medical systems include an inner tubular member defining an aperture and an outer tubular member at least partially surrounding the inner tubular member. The inner and outer tubular members can be arranged such that an implantable medical endoprosthesis can be disposed therebetween.

17 Claims, 12 Drawing Sheets

(56) References Cited

U.S. PATENT DOCUMENTS

| | | |
|---|---|---|
| 5,458,605 A | 10/1995 | Klemm |
| 5,484,444 A | 1/1996 | Braunschweiler et al. |
| 5,507,768 A | 4/1996 | Lau et al. |
| 5,533,968 A | 7/1996 | Muni et al. |
| 5,690,644 A | 11/1997 | Yurek et al. |
| 5,709,703 A | 1/1998 | Lukic et al. |
| 5,743,874 A | 4/1998 | Fischell et al. |
| 5,782,855 A | 7/1998 | Lau et al. |
| 5,843,028 A | 12/1998 | Weaver et al. |
| 5,921,971 A | 7/1999 | Agro et al. |
| 5,944,727 A * | 8/1999 | Ahari ............ A61F 2/962 606/108 |
| 5,980,533 A | 11/1999 | Holman |
| 6,007,522 A | 12/1999 | Agro et al. |
| 6,059,752 A | 5/2000 | Segal |
| 6,077,295 A | 6/2000 | Limon et al. |
| 6,113,607 A | 9/2000 | Lau et al. |
| 6,368,302 B1 | 4/2002 | Fitzmaurice et al. |
| 6,582,459 B1 | 6/2003 | Lau et al. |
| 6,592,549 B2 | 7/2003 | Gerdts et al. |
| 6,613,075 B1 | 9/2003 | Healy et al. |
| 6,723,071 B2 | 4/2004 | Gerdts et al. |
| 7,052,511 B2 * | 5/2006 | Weldon ............ A61F 2/95 606/194 |
| 2002/0120323 A1 * | 8/2002 | Thompson ............ A61F 2/91 623/1.11 |
| 2003/0093106 A1 | 5/2003 | Brady et al. |
| 2003/0109886 A1 | 6/2003 | Keegan et al. |
| 2003/0208221 A1 | 11/2003 | El-Nounou |
| 2004/0064136 A1 * | 4/2004 | Papineau ............ A61B 17/32002 606/41 |
| 2004/0092867 A1 | 5/2004 | Murray, III |
| 2004/0098081 A1 | 5/2004 | Landreville et al. |
| 2005/0090890 A1 * | 4/2005 | Wu ............ A61F 2/95 623/1.11 |
| 2005/0113902 A1 | 5/2005 | Geiser et al. |
| 2005/0149159 A1 * | 7/2005 | Andreas ............ A61F 2/95 623/1.11 |
| 2006/0100687 A1 | 5/2006 | Fahey et al. |
| 2006/0200221 A1 | 9/2006 | Malewicz |
| 2006/0282147 A1 | 12/2006 | Andreas |
| 2008/0114435 A1 | 5/2008 | Bowe |
| 2010/0087906 A1 | 4/2010 | Dorn et al. |

FOREIGN PATENT DOCUMENTS

| | | |
|---|---|---|
| JP | 63111833 U | 7/1988 |
| JP | 2002360706 A | 12/2002 |
| JP | 2004530507 A | 10/2004 |
| WO | 9949808 A1 | 10/1999 |
| WO | 0069498 A1 | 11/2000 |
| WO | 2007053187 A2 | 5/2007 |
| WO | 2007110224 A1 | 10/2007 |
| WO | 2008039846 A1 | 4/2008 |

* cited by examiner

MEDICAL SYSTEMS AND RELATED METHOD

RELATED PATENT DOCUMENTS

This is a continuation of U.S. patent application Ser. No. 14/300,334, filed Jun. 10, 2014, now U.S. Pat. No. 9,717,613, which is a continuation of U.S. patent application Ser. No. 12/022,513, filed Jan. 30, 2008, now U.S. Pat. No. 8,758,421, which are incorporated herein by reference.

TECHNICAL FIELD

This invention relates to medical systems and related methods.

BACKGROUND

Devices are known for delivering implantable endoprostheses, such as stents, into a body vessel. Devices of this kind often include a proximal portion that remains external to the body vessel during use and a distal portion that is inserted into the body vessel (e.g., through an incision). The proximal portion typically provides for manipulation of the device during use. The distal portion often includes an outer member slidably positioned about an inner tubular member with an endoprosthesis disposed therebetween. Generally, the distal portion of the device is advanced through the body vessel to a treatment site (e.g., a stenosis or aneurysm). The outer member can then be retracted to allow the endoprosthesis to expand to engage a wall of the body vessel at the treatment site. Thereafter, the device is removed leaving the endoprosthesis engaged with the body vessel.

SUMMARY

In one aspect of the invention, a system includes an outer tubular member defining a lumen, an inner tubular member extending within the lumen of the outer tubular member, and a support member disposed in a lumen of the inner tubular member. The inner tubular member has a sidewall defining an aperture configured to allow a guide wire to pass therethrough. The inner and outer tubular members are configured so that an implantable medical endoprosthesis can be disposed between the inner and outer tubular members. The support member is configured such that at least a portion of the support member can be disposed adjacent the aperture, and the support member and the outer tubular member are configured to retract relative to the inner tubular member.

In another aspect of the invention, a system includes an inner tubular member having a sidewall defining an elongate slot and an outer tubular member at least partially surrounding the inner tubular member. The inner tubular member is formed of one or more metals. The outer tubular member has a sidewall at least partially defining an opening arranged such that a guide wire can be passed through the elongate slot of the inner tubular member and the opening of the outer tubular member. The inner tubular member and the outer tubular member are arranged such that an implantable medical endoprosthesis can be disposed between the inner tubular member and the outer tubular member.

In an additional aspect of the invention, a system includes an inner tubular member extending within a lumen of an outer tubular member and a support member disposed in a lumen of the inner tubular member. The inner tubular member has a sidewall defining an aperture configured to allow a guide wire to pass through the aperture. The support member is configured so that at least a portion of the support member can be adjacent to the aperture. The support member and the outer tubular member are configured to retract relative to the inner tubular member.

In another aspect of the invention, a system includes an inner tubular member extending within a lumen of an outer tubular member from a proximal end of the outer tubular member toward a distal end of the outer tubular member. The inner tubular member is of unitary construction and has a sidewall defining an aperture configured to allow a guide wire to pass through the aperture. The outer tubular member and the inner tubular member are configured so that an implantable medical endoprosthesis can be disposed between the outer tubular member and the inner tubular member. The outer tubular member is retractable relative to the inner tubular member.

Embodiments can include one or more of the following features.

In some embodiments, the elongate slot extends longitudinally along the inner tubular member.

In certain embodiments, the elongate slot has a length greater than or equal to a length of an implantable medical endoprosthesis disposed between the outer tubular member and the inner tubular member distal to the elongate slot.

In some embodiments, the inner tubular member is of unitary construction.

In certain embodiments, the inner tubular member extends within a lumen of the outer tubular member from a proximal end of the outer tubular member toward a distal end of the outer tubular member.

In some embodiments, the inner tubular member is formed of the one or more metals.

In certain embodiments, a portion of the sidewall of the inner tubular member proximal to the elongate slot defines cuts.

In some embodiments, the cuts are in the form of an interrupted spiral.

In certain embodiments, a portion of the sidewall of the inner tubular member distal to the elongate slot defines at least one cut.

In some embodiments, at least one cut is in the form of a continuous spiral.

In certain embodiments, a distal cross-sectional area of the inner tubular member is greater than a proximal cross-sectional area of the inner tubular member.

In some embodiments, the system further includes a support member disposed in a lumen of the inner tubular member. The support member is configured so that at least a portion of the support member can be disposed adjacent the aperture. The support member is arranged to retract relative to the inner tubular member.

In certain embodiments, a distal end portion of the support member is configured to (e.g., shaped to) direct a guide wire toward the aperture when the guide wire is passed through a lumen of the inner tubular member in a proximal direction.

In some embodiments, the distal end portion of the support member is tapered.

In certain embodiments, the support member is longitudinally fixed relative to the outer tubular member.

In some embodiments, a distal end portion of the support member is fixed relative to the outer tubular member at a location adjacent the opening in the sidewall of the outer tubular member.

In certain embodiments, the support member includes a distal member secured to a pull wire.

In some embodiments, the support member is substantially rotationally fixed relative to the inner tubular member.

In certain embodiments, at least a portion of the support member has a non-circular cross-section and at least a portion of a lumen of the inner tubular member has a non-circular cross-section.

In some embodiments, at least a portion of the support member has a square cross-section and at least a portion of a lumen of the inner tubular member has a square cross-section.

In certain embodiments, the support member includes a radial projection configured to be received in a longitudinal channel defined by the inner tubular member.

In some embodiments, the system further includes a sleeve extending within a distal portion of the inner tubular member. The sleeve is configured to allow a guide wire to be passed through the sleeve.

In certain embodiments, the sleeve includes a polymer.

In some embodiments, the sleeve includes a polyimide.

In some embodiments, the sleeve is arranged to direct a guide wire into the aperture when the guide wire is passed through the sleeve in a proximal direction.

In certain embodiments, the sleeve includes a proximal portion (e.g., a proximal curved portion) that extends into the aperture.

In some embodiments, the system further includes an implantable medical endoprosthesis disposed between the inner tubular member and the outer tubular member.

In certain embodiments, the implantable medical endoprosthesis is a self-expanding implantable medical endoprosthesis.

In some embodiments, the implantable medical endoprosthesis is disposed distal to the elongate slot.

In certain embodiments, the aperture is a longitudinally extending elongate slot.

In some embodiments, the implantable medical endoprosthesis is disposed distal to the aperture.

Embodiments can include one or more of the following advantages.

In some embodiments, the elongate slot of the inner tubular member is configured so that a guide wire can extend radially through the elongate slot and through an opening in the outer sheath during use. The elongate slot can permit the outer tubular assembly to be retracted relative to the inner tubular member and the guide wire without substantial resistance. For example, the elongate slot can be arranged to inhibit the guide wire extending therethrough from getting pinched between the outer tubular assembly and the inner tubular member as the outer tubular member is retracted relative to the inner tubular member.

In certain embodiments, the inner tubular member is a continuous member of unitary construction. As a result, the inner tubular member can be manufactured relatively simply and inexpensively.

In some embodiments, the support member is disposed within the inner tubular member adjacent the elongate slot in the inner tubular member. The support member can thus support the portion of the inner tubular member including the elongate slot and inhibit that portion of the outer tubular member from kinking.

In certain embodiments, the support member is arranged to be retracted along with the outer sheath of the outer tubular assembly to allow the location at which the guide wire passes radially through the slot to move proximally as the outer sheath is proximally retracted. The retracting support member can inhibit the guide wire from becoming pinched between the outer sheath of the outer tubular assembly and the support member as the outer sheath is retracted. This arrangement can thus help to ensure that the outer sheath can be retracted sufficiently to fully deploy the endoprosthesis.

In some embodiments, the flexibility of the inner tubular member gradually increases (i.e., does not change abruptly) in the distal direction. As a result, the inner tubular member can exhibit improved distal pushability. For example, the inner tubular member can be less prone to hinging and prolapsing as it is navigated through a vessel.

In certain embodiments, the inner tubular member includes one or more portions with material removed from the inner tubular member. The inner tubular member can, for example, include proximal and distal portions with one or more apertures (e.g., a pattern of apertures). The apertures can be arranged to provide the proximal portion of the inner tubular member with a relatively high compressive strength and the distal portion of the inner tubular member with a relatively high level of flexibility. This arrangement can improve the ability of the system to be navigated through tortuous body vessels.

Other features and advantages are in the description, drawings, and claims.

DETAILED DESCRIPTION

Figure 1:
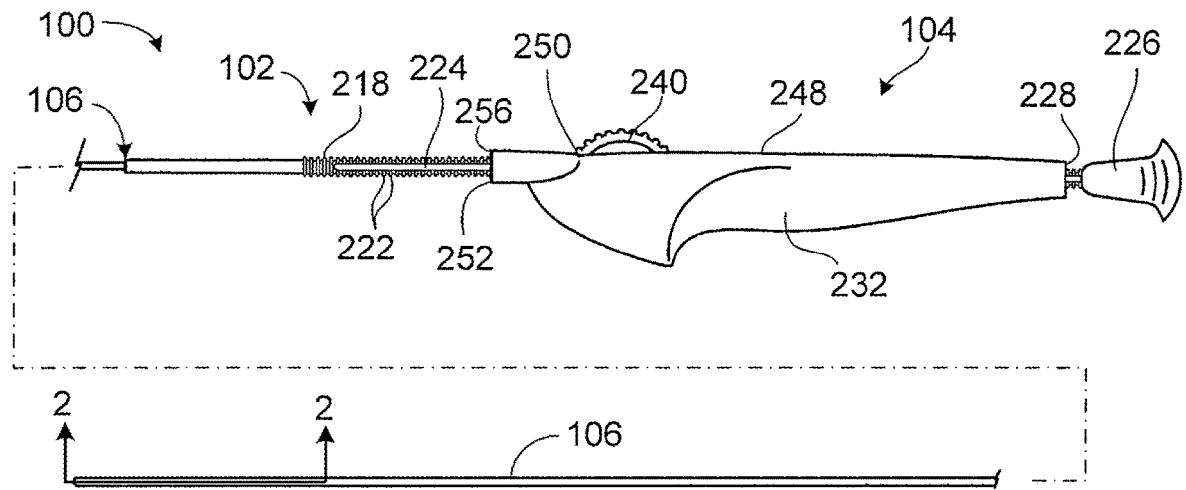
FIG. 1 is a broken, side view of a self-expanding stent delivery system.
Figure 2:
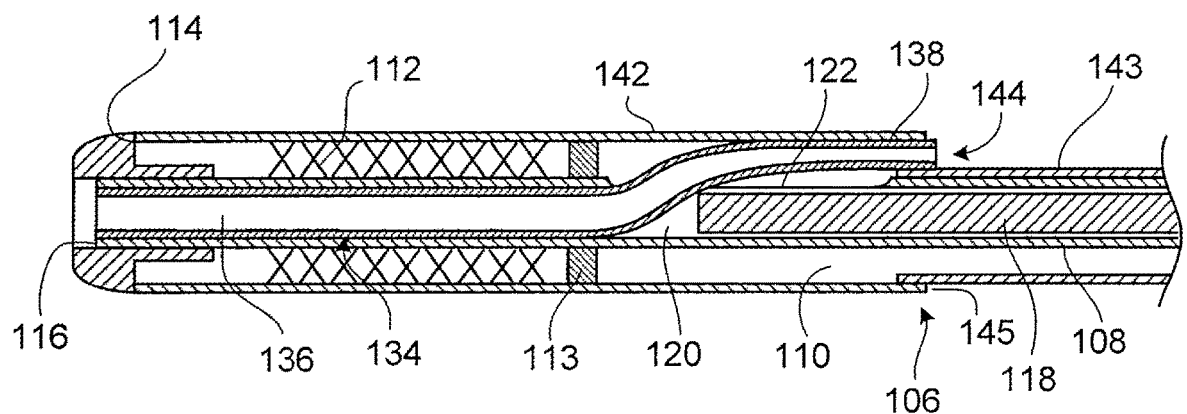
FIG. 2 is a cross-sectional view of a distal region of the self-expanding stent delivery system of FIG. 1, taken along line 2-2 in FIG. 1.

Referring to FIGS. 1 and 2, a stent delivery system 100 includes a catheter assembly 102 and a handle assembly 104. Catheter assembly 102 includes an outer tubular assembly 106 and an inner tubular member 108 extending through a lumen 110 formed by outer tubular assembly 106. A support member 118 extends along an inner lumen 120 formed by inner tubular member 108. A self-expanding stent 112 is disposed between outer tubular assembly 106 and inner tubular member 108, near distal ends 114, 116 of outer tubular assembly 106 and inner tubular member 108. A bumper 113 extends radially from inner tubular member 108 slightly proximal to stent 112. During use, as described in more detail below, a distal portion of catheter assembly 102 can be disposed within a body vessel (e.g., a blood vessel) of a patient, and outer tubular assembly 106 and support member 118 can be moved proximally relative to inner tubular member 108 to deploy stent 112 within the body vessel.

Figure 3:
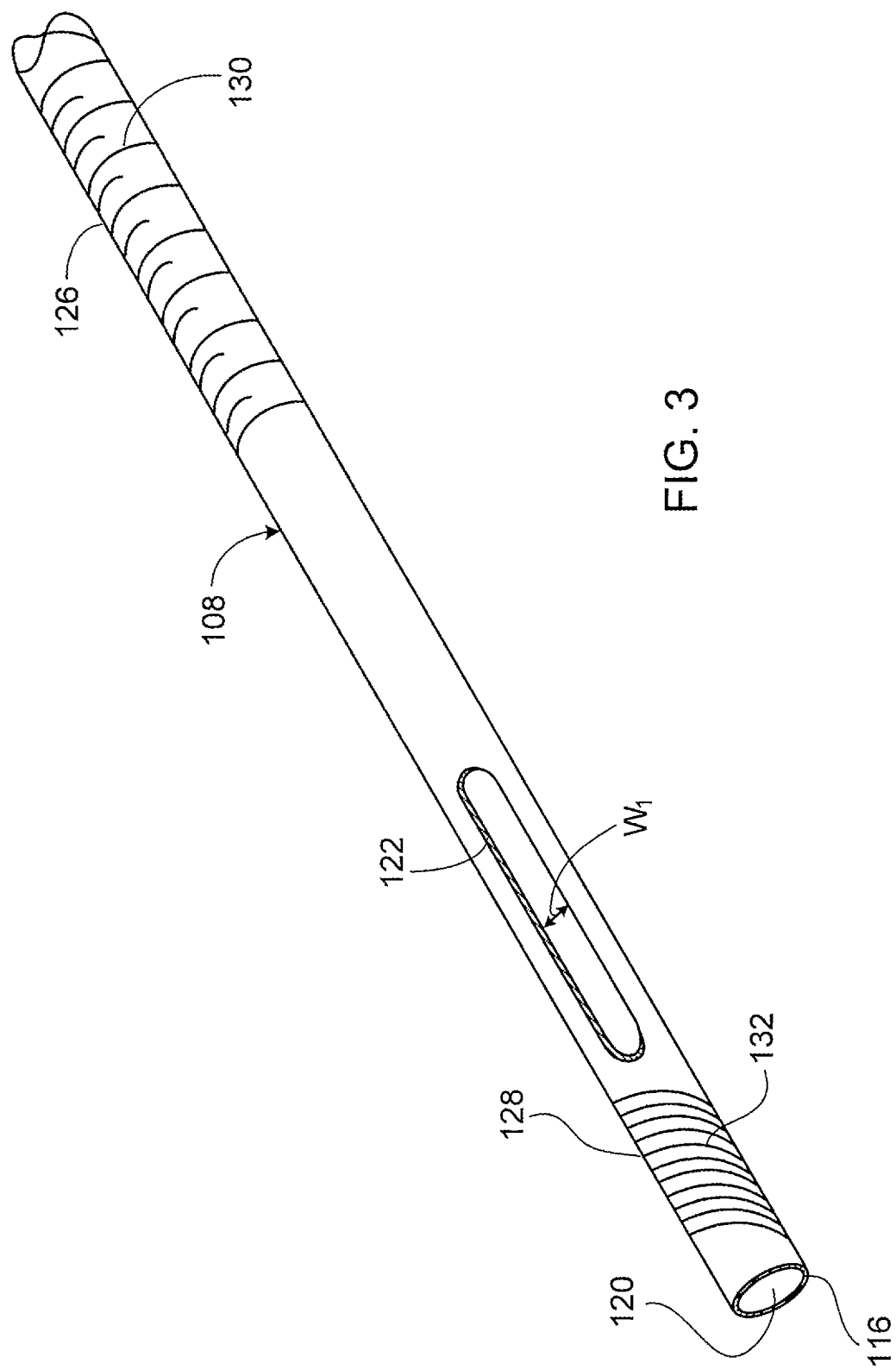
FIG. 3 is a perspective view of the inner tubular member of FIG. 2.

FIG. 3 illustrates a perspective view of inner tubular member 108. Inner tubular member 108 is of unitary construction and is formed of stainless steel. Inner tubular member 108 includes inner lumen 120, which has a substantially circular cross-section along the longitudinal axis of inner tubular member 108. An elongate slot 122 is formed in the sidewall of inner tubular member 108. Elongate slot 122 has a width $W_1$ that is at least large enough to allow a guide wire 124 to pass therethrough. Width $W_1$ can, for example, be about 0.4 millimeters or greater (e.g., about 0.5 millimeters or greater). In certain embodiments, Width $W_1$ is about 0.4 millimeters to about 1.0 millimeter (e.g., about 0.6 millimeters to about 0.8 millimeters). Elongate slot 122 extends generally parallel to the longitudinal axis of inner tubular member 108. As will be described in further detail below, the length of elongate slot 122 is typically greater than or equal to a longitudinal dimension of stent 112. In some embodiments, slot 122 has a length of about 20 millimeters or more (e.g., about 60 millimeters or more). In certain embodiments, slot 122 has a length of about 20 millimeters to about 310 millimeters (e.g., about 30 millimeters to about 300 millimeters).

The distal end of elongate slot 122 can be spaced from distal end 116 of inner tubular member 108 by about 30 millimeters or more (e.g., about 70 millimeters or more). In certain embodiments, the distal end of elongate slot 112 is spaced from distal end 116 of inner tubular member 108 by about 30 millimeters to about 320 millimeters (e.g., about 40 millimeters to about 310 millimeters).

Material can be removed from a substantial portion of the circumference of inner tubular member 108 to form elongate slot 122. In some embodiments, for example, material is removed from about 30 percent or more (e.g., about 40 percent or more, about 50 percent or more, about 60 percent or more) of the circumference of inner tubular member 108 to form elongate slot 122. In certain embodiments, material is removed from about 40 percent to about 60 percent (e.g., about 50 percent) of the circumference of inner tubular member 108 to form elongate slot 122.

Elongate slot 122 can be formed in inner tubular member 108 using any of various material removal techniques. In certain embodiments, for example, the sidewall of inner tubular member 108 is skived to form elongate slot 122. In such embodiments, elongate slot 122 can have a longitudinal cross-section substantially formed in the shape of a trough. Elongate slot 122 can alternatively or additionally be formed by using laser machining to remove material from inner tubular member 108 such that inner lumen 120 becomes exposed. In addition or in the alternative, elongate slot 122 can be formed using wire electrical discharge machining (EDM).

Inner tubular member 108 further includes a first portion 126 proximal to elongate slot 122 and a second portion 128 distal to elongate slot 122. First portion 126 includes multiple apertures (e.g., slits or cuts) 130 that extend through the sidewall of inner tubular member 108. Apertures 130 are arranged in the form of an interrupted spiral. As a result, apertures 130 increase the flexibility of inner tubular member 108 along first portion 126 while allowing first portion 126 to remain pushable in the distal direction. For example, those regions of first portion from which material has been removed provide enhanced flexibility while the portions therebetween from which no material has been removed enhance pushability by inhibiting compression of inner tubular member 108. Second portion 128 includes an aperture (e.g., a slit or cut) 132 that extends through the sidewall of inner tubular member 108. Aperture 132 is arranged in the form of an uninterrupted spiral extending along the distal portion of inner tubular member 108. The spiral path from which material has been removed increases the flexibility of inner tubular member 108 along second portion 128. As a result of spiral aperture 132, second portion 128 of inner tubular member 108 has greater flexibility than first portion 126 of inner tubular member 108. The increased flexibility of second portion 128 relative to first portion 126 allows second portion 128 to traverse tortuous regions of body vessels during use. Similarly, the high level of stiffness of first portion 126 relative to second portion 128 enhances the overall pushability of inner tubular member 108.

Apertures 130, 132 can be configured to achieve any of various different desired flexibility characteristics of inner tubular member 108. For example, the pitch of the spiral of apertures 130 and 132 can be decreased to increase the flexibility of first and second portions 126 and 128, respectively. Similarly, the pitch of the spiral of apertures 130 and 132 can be increased to increase the rigidity and pushability of first and second portions 126 and 128, respectively. As another example, the distance between adjacent apertures 130 in the interrupted spiral pattern in first portion 126 can be increased to increase the distal pushability of first portion 126 and can be decreased to increase flexibility of first portion 126. In some embodiments, the pitch of the spiral of aperture(s) 130 and/or 132 decreases in the distal direction, resulting in increased flexibility in the distal direction along aperture(s) 130 and/or 132. Apertures 130, 132 can be formed in the sidewall of inner tubular member 108 using any of various material removal techniques. For example, a laser can be used to cut apertures 130, 132 into the sidewall of inner tubular member 108. Alternatively or additionally, EDM techniques or mechanical material removal techniques can be used.

Referring again to FIG. 2, support member 118 is disposed within inner lumen 120 of inner tubular member 108 in a region of inner lumen 120 that is adjacent elongate slot and slightly proximal to the location at which a polymeric sleeve 134 exits elongate slot 122. Due to the reduced amount of material in the portion of inner tubular member including elongate slot 122, this portion of inner tubular member 108 tends to be more flexible than the region directly adjacent (e.g., directly proximal or directly distal) to it. In some instances, the portion of inner tubular member 108 that includes elongate slot 122 has a greater flexibility than first and second portions 126 and 128 of inner tubular member 108. The presence of support member 118 in the region of lumen 120 adjacent elongate slot 122 stiffens inner tubular member 108 and inhibits buckling of inner tubular member 108. As will be described in further detail below, when outer tubular assembly 106 is retracted to deploy stent 112, the distal end of support member 118 moves proximally within inner lumen 120 adjacent elongate slot 122, which allows the location at which the guide wire exits elongate slot 122 (i.e., via polymeric sleeve 134) to move proximally during the process.

Support member 118 is a solid member (e.g., a solid wire or a mandrel) that is movable along the longitudinal axis of inner lumen 120. The outer surface of support member 118 contacts the inner surface of inner tubular member 108 in the region of inner tubular member 108 that includes elongate slot 122 and in the region of inner tubular member 108 proximal to elongate slot 122. This contact between support member 118 and inner tubular member 108 provides inner tubular member with radial support, which can inhibit inner tubular member 108 from kinking when compressive forces are applied to it during use. This contact between support member 118 and inner tubular member 108 also prevents distortion or deformation of inner tubular member 108 along elongate slot 122.

An outer diameter of support member 118 and an inner diameter of inner tubular member 108 can be dimensioned to inhibit air from traveling through inner lumen 120 (e.g., to reduce the need to flush the portion of inner tubular member 108 proximal to elongate slot 122). In some embodiments, the clearance between the outer diameter of support member 118 and the inner diameter of inner tubular member 108 is 0.05 millimeters or less. In certain embodiments, the clearance between the outer diameter of support member 118 and the inner diameter of inner tubular member 108 is about 0.025 millimeters to about 0.05 millimeters (e.g., about 0.03 millimeters to about 0.04 millimeters).

Support member 118 can be made of any of various materials. For example, support member 118 can include one or more metals or alloys, such as stainless steel or Nitinol. In addition or in the alternative, support member 118 can include one or more relatively rigid polymers, such as polyetheretherketone (PEEK) polymers, nylon, polyimides, high durometer polyether block amides (e.g., PEBAX®70D, PEBAX® 72D). In some embodiments, the distal end portion of support member 118 includes one or more relatively rigid materials while the proximal end portion of support member 118 includes more flexible materials.

Referring still to FIG. 2, polymeric sleeve 134 extends proximally from distal end 116 of inner tubular member 108 and extends radially through elongate slot 122. A proximal end region 138 of sleeve 134 extends into a port 144 formed by outer tubular assembly 106. Sleeve 134 contacts a portion of outer tubular assembly 106 (e.g., in the region of port 144) but is not bonded to outer tubular assembly 106. This arrangement allows outer tubular assembly 106 to be retracted relative to sleeve 134. As will be discussed in further detail below, during use, a guide wire extends through a lumen 136 in sleeve 134. Sleeve 134 helps to direct the guide wire toward port 144 and also helps to prevent metal to metal contact between guide wire 124 and the sidewall of inner lumen 120. Sleeve 134 can also inhibit direct contact between guide wire 124 and support member 118, which can reduce friction between the guide 124 and support member 118. By inhibiting direct contact between guide wire 124 and support member 118, sleeve 134 can also reduce surface changes (e.g., scratches, etc.) to the guide wire. Sleeve 134 can be formed of any of various different polymers, such as polyimides, polytetrafluoroethylene (PTFE), polyethylenes, and nylons. In certain embodiments, the inner surface of sleeve 134 can include a lubricious coating to reduce friction between sleeve 134 and a guide wire that passes therethrough. Examples of lubricious coatings include fluoropolymer (e.g., PTFE) coatings, silicone coatings, ultrahigh molecular weight polyethylene coatings, oil coatings, and coatings formed of blends of two or more of the previously mentioned materials.

Still referring to FIG. 2, outer tubular assembly 106 includes a proximal outer sheath 143 secured to the distal end of a tubular rack 218 (shown in FIG. 1) and bonded to the proximal end region of a distal outer sheath 142. Proximal outer sheath 143 is arranged over inner tubular member 108. Distal outer sheath 142, which extends distally from proximal outer sheath 143, surrounds stent 112 to retain stent 112 in an unexpanded state when outer tubular assembly 106 is in a fully distal position, as shown in FIG. 2. As described in further detail below, distal and proximal outer sheaths 142, 143 are retractable together in the proximal direction to release stent 112.

A portion of the outer circumference of proximal outer sheath 143 is attached (e.g., thermally bonded, adhesively bonded, etc.) to at least a portion of the inner circumference of distal outer sheath 142 to form a joint 145. At joint 145, the outer diameter of proximal outer sheath 143 is smaller than the inner diameter of distal outer sheath 142, forming port 144, which accommodates proximal end region 138 of sleeve 134.

Distal and proximal outer sheaths 142, 143 can each be flexible along the longitudinal axis of catheter assembly 102. For example, distal and proximal outer sheaths 142, 143 can include one or more compliant polymeric materials. Examples of suitable polymeric materials include polyetherblock co-polyamide polymers (e.g., PEBAX®), copolyester elastomers (e.g., Arnitel® copolyester elastomers), thermoplastic polyester elastomers (e.g., Hytrel®), thermoplastic polyurethane elastomers (e.g., Pellethane™), polyolefins (e.g., Marlex® polyethylene, Marlex® polypropylene), high-density polyethylene (HDPE), low-density polyethylene (LDPE), polyamides (e.g., Vestamid® and combinations of these materials. In certain embodiments, inner tubular member 108 and distal and proximal outer sheaths 142, 143 include one or more silicones. In certain embodiments (e.g., when it is desirable to reduce force used to retract distal and proximal outer sheaths 142, 143), distal and proximal outer sheaths 142, 143 can be made of a material having a relatively low coefficient of friction (e.g., a fluoropolymer or a silicone). Examples of fluoropolymers include PTFE and FEP. Alternatively or additionally, distal and proximal outer sheaths 142, 143 can be made of a material that includes a lubricious additive (e.g., a fluoropolymer, a silicone, an ultrahigh molecular weight polyethylene, an oil, or blends thereof). In some embodiments, distal outer sheath 142 can be formed of a different material than proximal outer sheath 143. In such embodiments, for example, distal outer sheath 142 can be formed of a more flexible material than proximal outer sheath 143.

Referring again to FIG. 1, outer tubular assembly 106 of catheter assembly 102, further includes tubular rack 218, which is attached to the proximal end of proximal outer sheath 143. Tubular rack 218 includes multiple radially extending teeth 222 that are axially spaced apart along tubular rack 218. A longitudinal slot 224 is formed in the sidewall of tubular rack 218. Slot 224 provides a radial passage from lumen 110 of outer tubular assembly 106 to an area surrounding tubular rack 218. A pull grip 226 is provided on a proximal end region of tubular rack 218. Pull grip 226 is located proximal to a proximal end 228 of handle assembly 104 and includes radially extending projections that can be grasped by the user.

Figure 4:
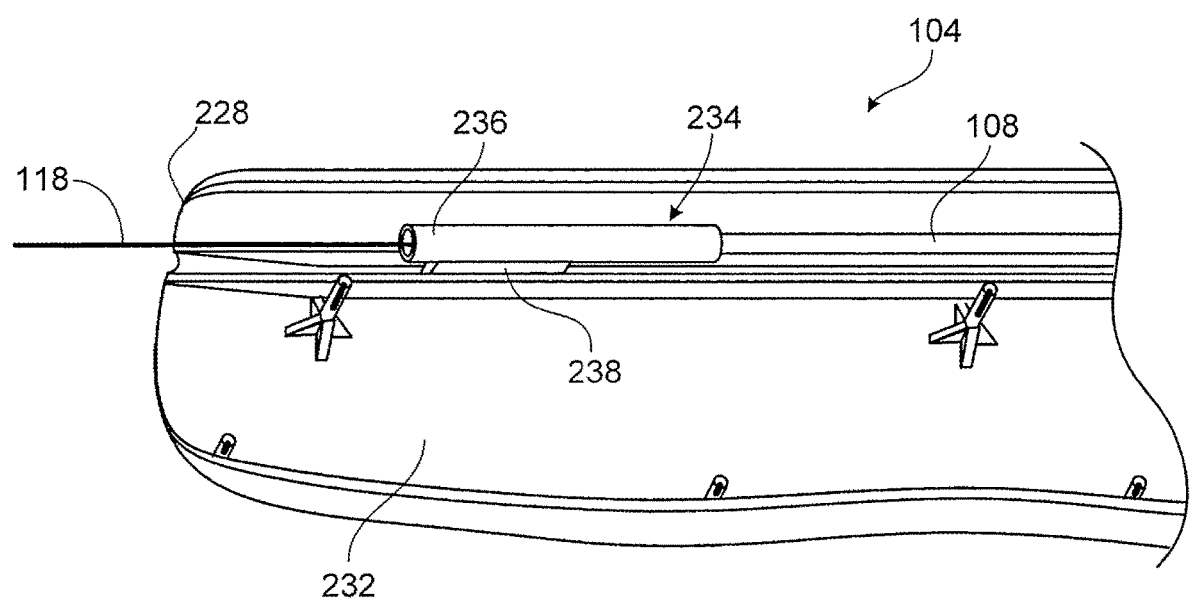
FIG. 4 illustrates a connection between the inner tubular member of the catheter assembly and the housing of the handle assembly of the self-expanding stent delivery system of FIG. 1.

FIG. 4 illustrates a section of handle assembly 104 in a partially assembled state with one of the sides of housing 232 removed to show how inner tubular member 108 is secured to housing 232. As shown in FIG. 4, inner tubular member 108 is secured to an inner surface of housing 232 by a connector 234 near the proximal end of housing 232. Connector 234 includes a tubular segment 236 through which inner tubular member 108 partially extends. Inner tubular member 108 is attached (e.g., welded, thermally bonded, adhesively bonded) to the inner surface of tubular segment 236. A rib portion 238 extends radially outwardly from tubular segment 236 and is attached (e.g., welded, thermally bonded, adhesively bonded, insert molded) to the inner surface of the side wall of housing 232 of handle assembly 104. As a result, connector 234 and inner tubular member 108 are axially fixed relative to housing 232.

Figure 5:
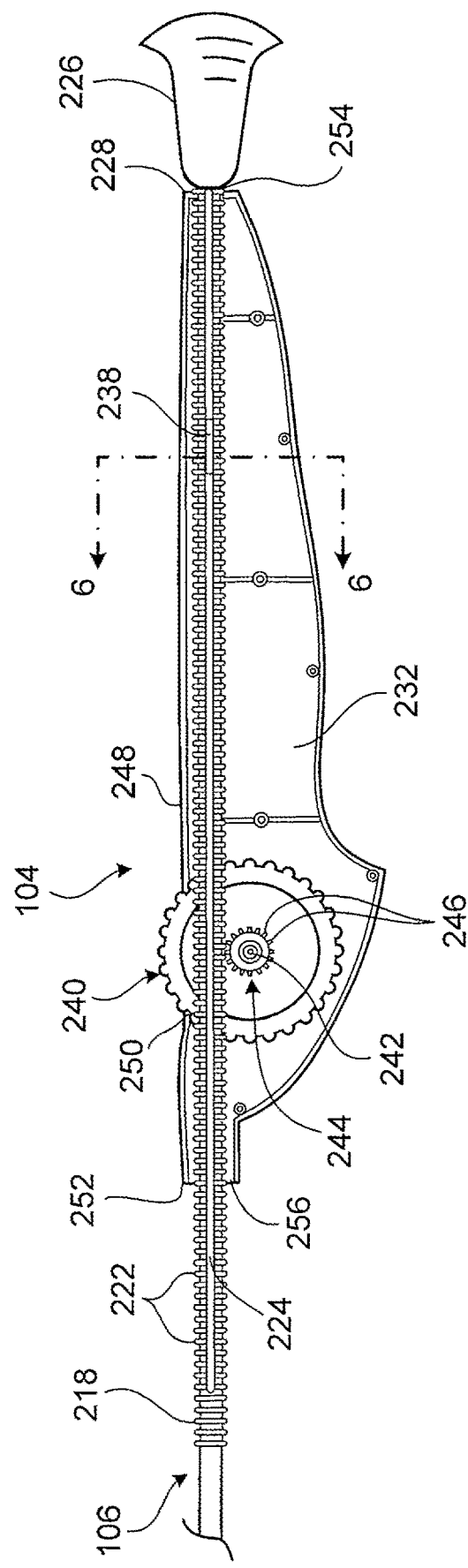
FIG. 5 is a side view of the handle assembly of the self-expanding stent delivery system of FIG. 1 in an operative configuration with the near side of its housing removed to expose certain interior components of the handle assembly.

FIG. 5 illustrates a side view of handle assembly 104 in an operable configuration with the near side of its housing 232 (i.e., the side of housing 232 to which connector 234 is secured, as shown in FIG. 4) removed to expose certain interior components of handle assembly 104. As shown in FIG. 5, a rotatable knob 240 is rotatably mounted to housing 232. Rotatable knob 240 includes a pin 242 that extends laterally from a side surface of rotatable knob 240 and can be disposed within a cylindrical recess defined by the side wall housing 232. Rotatable knob 240 also includes a gear 244 that laterally extends from the side surface of rotatable knob 240. Gear 244 includes multiple circumferentially spaced teeth 246 that extend radially from a peripheral surface of gear 244. A top wall 248 of housing 232 includes an aperture 250 through which an upper portion of rotatable knob 240 protrudes to allow rotatable knob 240 to be rotated by the thumb of a user.

Referring to FIGS. 4 and 5, support member 118 extends through inner tubular member 108 and beyond connector 234 in the proximal direction. Support member 118 is axially movable relative to housing 232, while inner tubular member 108 is axially fixed relative to housing 232. Thus, in use, support member 118 is retractable relative to inner tubular member 108. Support member 118 is attached (e.g., welded, thermally bonded, adhesively bonded, etc.) to a portion of tubular rack 218 proximal to connector 234. As a result, support member 118 is retracted when tubular rack 218 is retracted. In certain embodiments, the outer surface of support member 118 is attached to the inner surface of tubular rack 218 proximal to connector 234. A proximal end region of support member 118 can alternatively or additionally be attached to pull grip 226.

Referring still to FIGS. 4 and 5, in the operable configuration, inner tubular member 108, support member 118, and tubular rack 218 of catheter assembly 102 extend within a cavity formed by housing 232 of handle assembly 104. Teeth 222 of tubular rack 218 mate with teeth 246 of gear 244. Thus, tubular rack 218, as well as support member 118 which is fixed to tubular rack 218, can be axially displaced by rotating rotatable knob 240. Tubular rack 218 extends entirely through handle assembly 104 such that, in an initial configuration, a proximal region of tubular rack 218 extends proximal to a proximal end 228 of handle assembly 104 and a distal region of tubular rack 218 extends distal to distal end 252 of handle assembly 104. Housing 232 of handle assembly 104 includes proximal and distal openings 254, 256 that provide sufficient clearance for tubular rack 218, support member 118, and proximal outer sheath 143 to pass through the openings and thus move axially through housing 232 without substantial interference.

Figure 6:
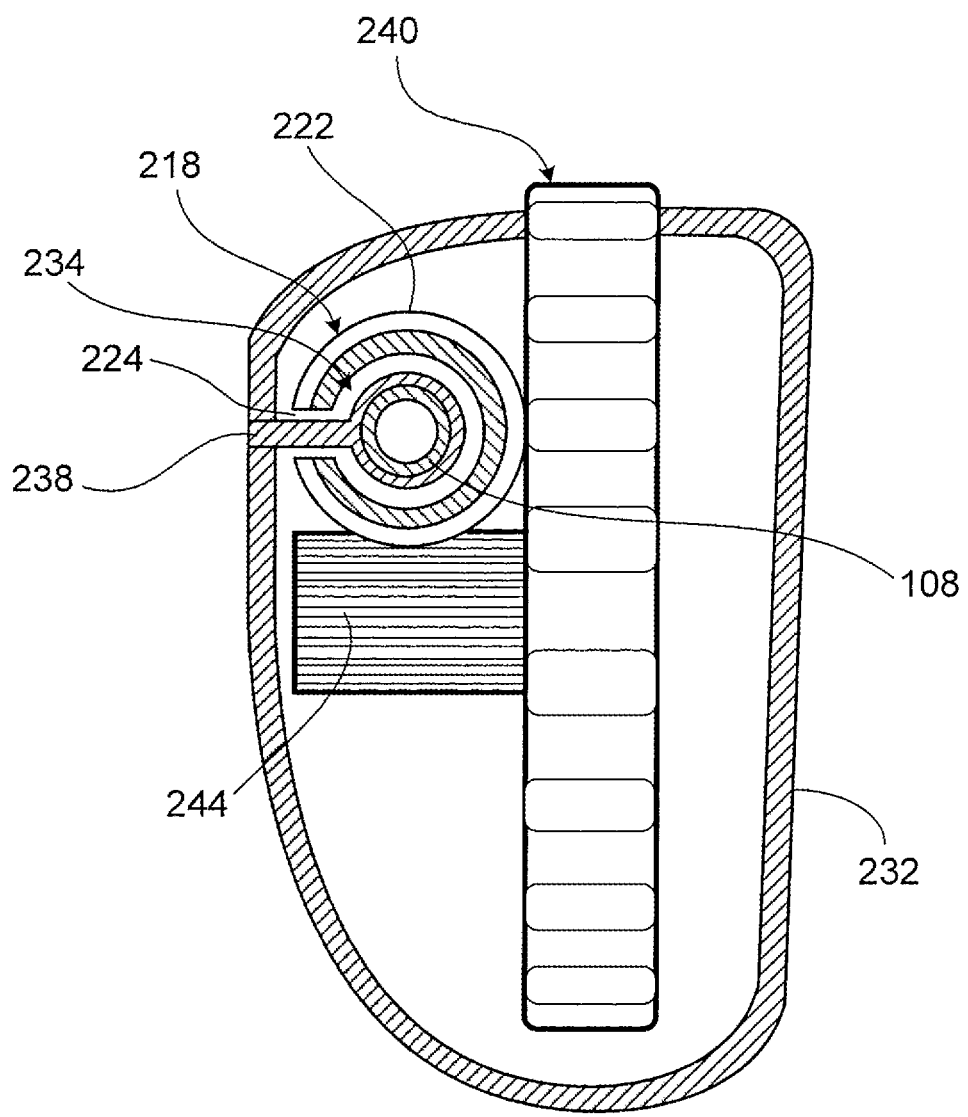
FIG. 6 is a cross-sectional view of the handle assembly of the self-expanding stent delivery system of FIG. 5 in a fully assembled configuration, taken along line 6-6 in FIG. 5.

FIG. 6 illustrates a cross-sectional view of handle assembly 104 in a fully assembled configuration (i.e., with the near side of housing 232 in place). As shown in FIG. 6, rib portion 238 of connector 234 extends radially through slot 224 of tubular rack 218. Slot 224 is configured (e.g., sized and shaped) so that tubular rack 218 can be retracted relative to connector 234 while rib portion 238 extends through slot 224.

Referring to FIGS. 5 and 6, slot 224 extends from the proximal end of tubular rack 218 to a location proximal to the distal end of tubular rack 218. As a result, tubular rack 218 can be proximally retracted until rib portion 238 of connector 234 abuts the distal end of slot 224. Due to the arrangement of slot 224, when outer tubular assembly 106 and support member 118 are fully retracted, the distal end of tubular rack 218 is located proximal to proximal end 228 of handle assembly 104 and portions of proximal outer sheath 143 and support member 118 are retracted into housing 232 of handle assembly 104.

Distal and proximal outer sheaths 142, 143 and support member 118 can be simultaneously retracted using either rotatable knob 240 or pull grip 226. To retract distal and proximal outer sheaths 142, 143 and support member 118 using rotatable knob 240, the user rotates rotatable knob 240 in a clockwise direction (in the view illustrated in FIG. 5). The rotation of gear 244 causes teeth 246 of gear 244 to engage teeth 222 of tubular rack 218, and thereby proximally displace tubular rack 218. Because tubular rack 218 is secured to proximal outer sheath 143 and support member 118, the proximal displacement of tubular rack 218 results in retraction of distal and proximal outer sheaths 142, 143 and support member 118 at the same rate. To retract distal and proximal outer sheaths 142, 143 and support member 118 using pull grip 226, the user grasps pull grip 226 and pulls pull grip 226 in the proximal direction.

Figure 7A:
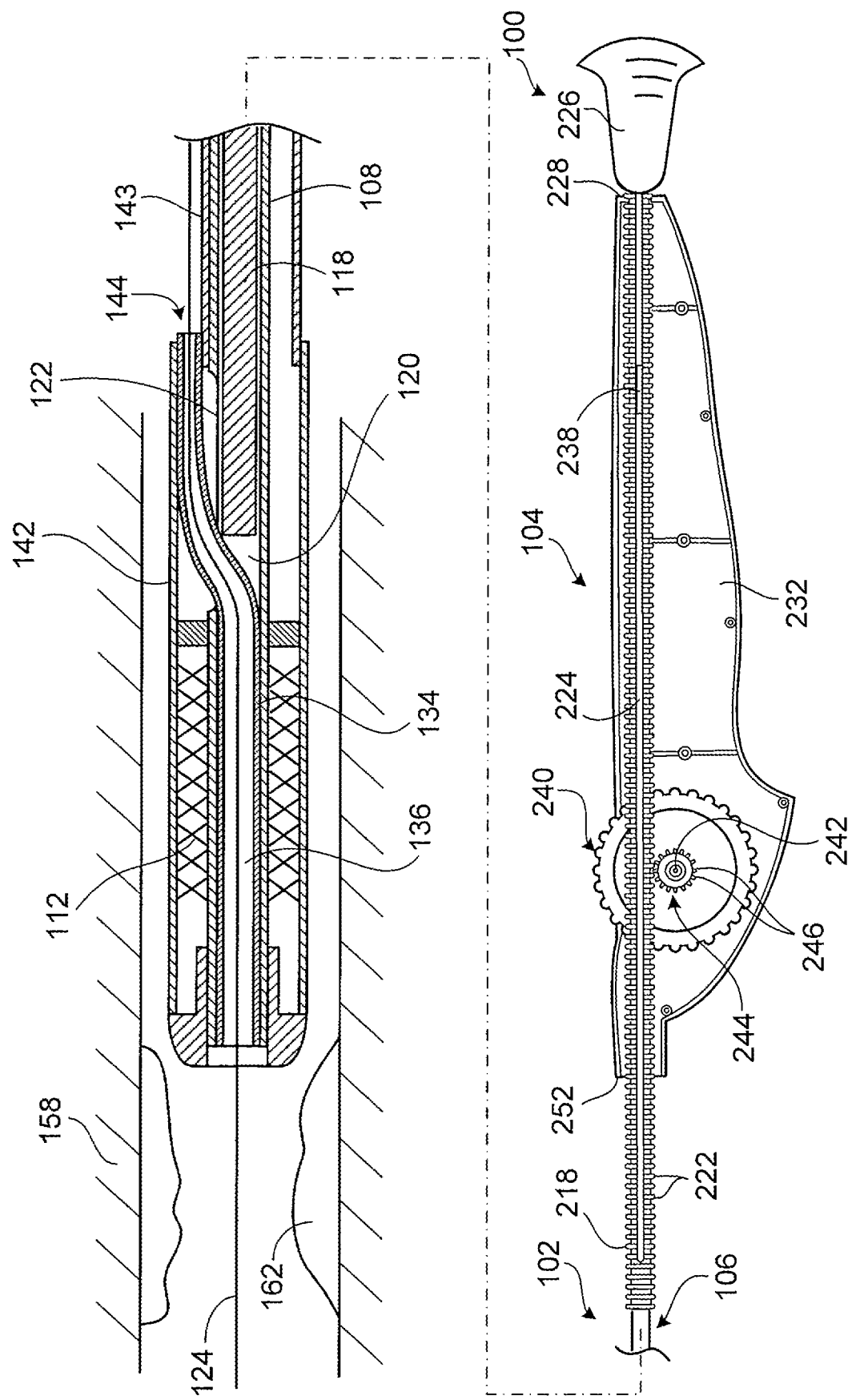
FIGS. 7A-7D illustrate a method of using the self-expanding stent delivery system of FIG. 1 to implant a self-expanding stent within a blood vessel.

FIGS. 7A-7D illustrate a method of using system 100 to implant stent 112 within a blood vessel 158 of a patient. Referring to FIG. 7A, guide wire 124 is first inserted into blood vessel 158, and catheter assembly 102 is passed over guide wire 124 toward a treatment site. To pass catheter assembly 102 over guide wire 124, the proximal end of guide wire 124 is first inserted into lumen 136 of polymeric sleeve 134 via distal openings in polymeric sleeve 134 and inner tubular member 108. Catheter assembly 102 is then backloaded onto guide wire 124 by passing the distal end portion of inner tubular member 108 over the proximal end portion of guide wire 124. As inner tubular member 108 is further passed over guide wire 124 in the distal direction, guide wire 124 passes through sleeve 134, exits elongate slot 122, and exits catheter assembly 102 via port 144. Guide wire 124 exits elongate slot 122 with sleeve 134 disposed between guide wire 124 and the sidewall of inner tubular member 108 that defines elongate slot 122. Sleeve 134 provides a path for guide wire 124 to follow through catheter assembly 102. Sleeve 134 inhibits metal-to-metal contact between guide wire 124 and the sidewall of inner tubular member 108. Proximal to port 144, guide wire 124 extends along the exterior surface of catheter assembly 102. A distal portion of catheter assembly 102 is navigated through blood vessel 158 and toward an occluded region 162 of blood vessel 158 by passing catheter assembly 102 over guide wire 124.

Figure 7B:
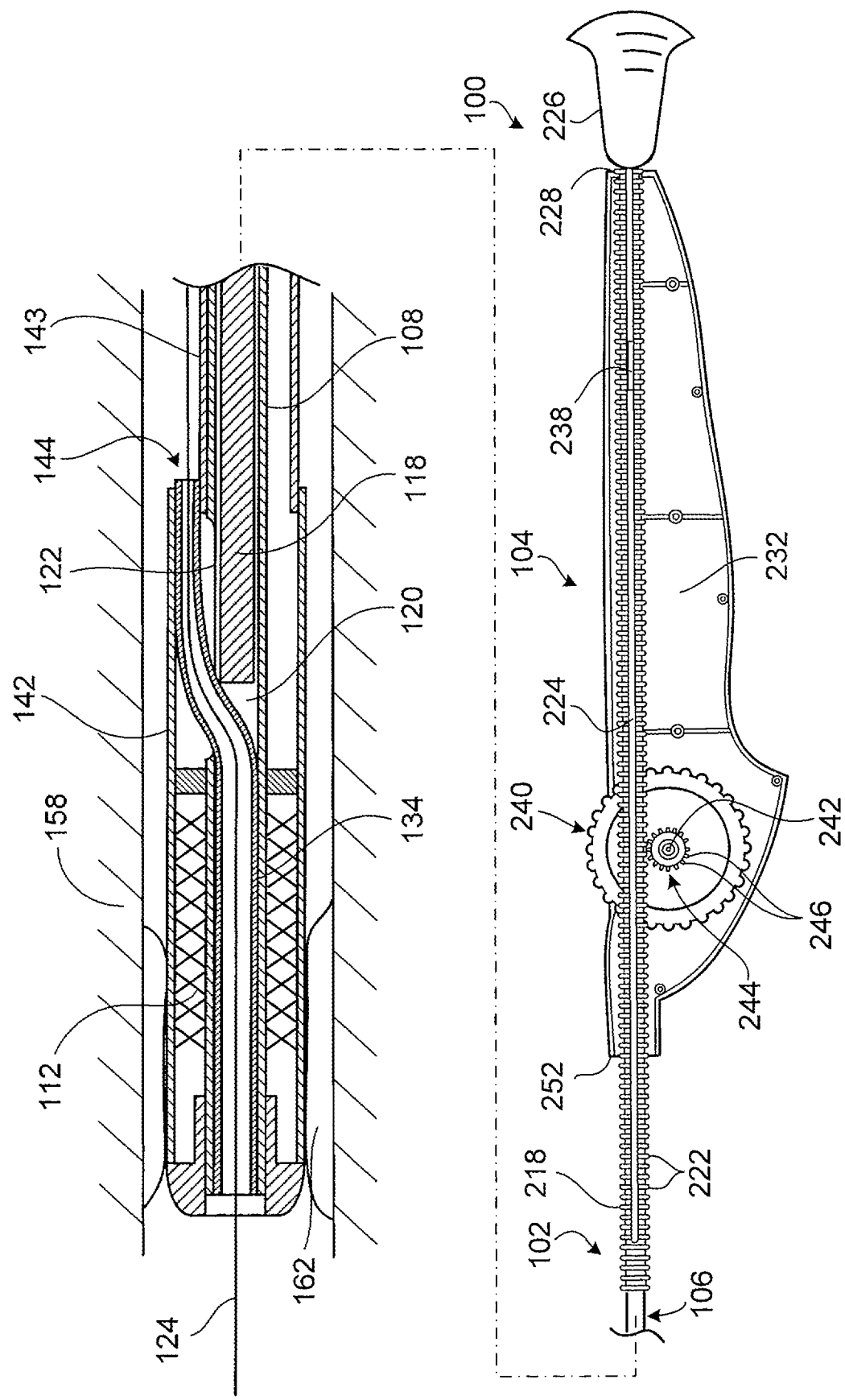

The distal portion of catheter assembly 102 is navigated through blood vessel 158 until the stent-carrying portion of catheter assembly 102 is positioned within occluded region 162 of blood vessel 158, as shown in FIG. 7B. Fluoroscopy or any of various other imaging techniques can be used to help the user position the stent-carrying portion of catheter assembly 102 within occluded region 162.

Figure 7C:
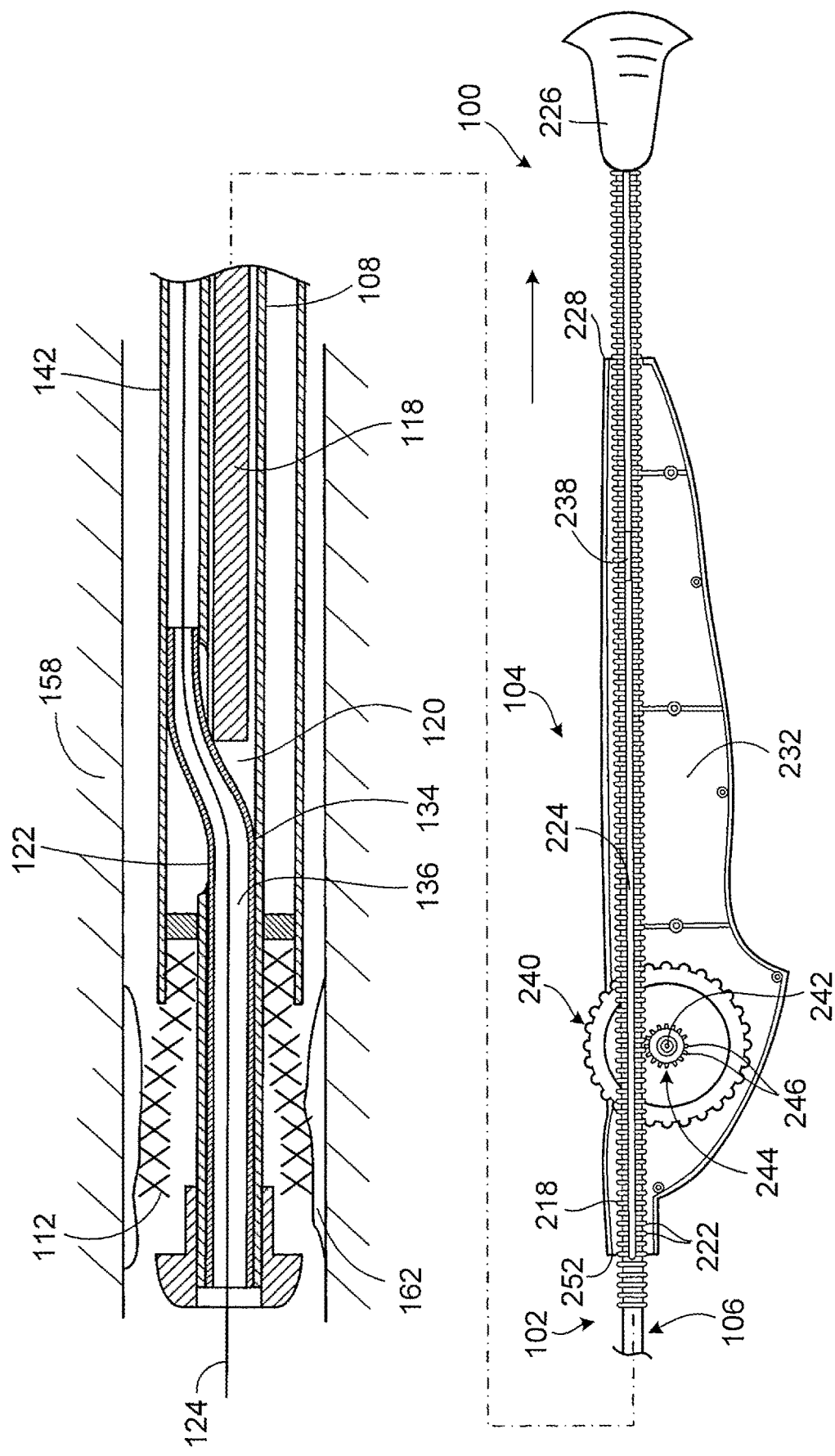

Referring to FIG. 7C, after positioning the stent-carrying portion of catheter assembly 102 within occluded region 162, tubular rack 218, support member 118, and distal and proximal outer sheaths 142, 143 are retracted an initial distance relative to inner tubular member 108 by rotating rotatable knob 240 in a clockwise direction (in the view illustrated in FIG. 7C). This initial retraction of distal outer sheath 142 allows a distal portion of stent 112 to self-expand within occluded region 162 and contact a wall of body vessel 158. Retraction of tubular rack 218 moves distal and proximal outer sheaths 142, 143 proximally relative to inner tubular member 108 and guide wire 124. In addition, because support member 118 is fixed to tubular rack 218, support member 118 also moves proximally within lumen 120 of inner tubular member 108. As support member 118 retracts, the point of contact between sleeve 134 and the distal end of support member 118 moves proximally, allowing sleeve 134 to change orientation such that an increased portion of sleeve 134 extends into inner lumen 120. The portion of guide wire 124 disposed within sleeve 134 changes profile along with sleeve 134, while guide wire 124 remains substantially fixed in the longitudinal direction. For example, sleeve 134 and a portion of guide wire 124 disposed therein can initially form substantially "s" shaped profiles and, as support member 118 retracts, the inflection points of the "s" shaped profiles move proximally. As the inflection points of sleeve 134 and guide wire 134 move proximally, sleeve 134 and guide wire 124 remain substantially, longitudinally fixed relative to inner tubular member 108.

This proximal movement of support member 118 inhibits sleeve 134 and/or guide wire 124 from becoming pinched between distal outer sheath 142 and the distal end of support member 118. This arrangement helps to ensure that distal outer sheath 142 can be retracted a sufficient distance to fully deploy stent 112. In addition, as discussed above, sleeve 134 inhibits contact between guide wire 124 and inner tubular member 108 as guide wire 124 changes profile (e.g., as described above) along elongate slot 122.

Figure 7D:
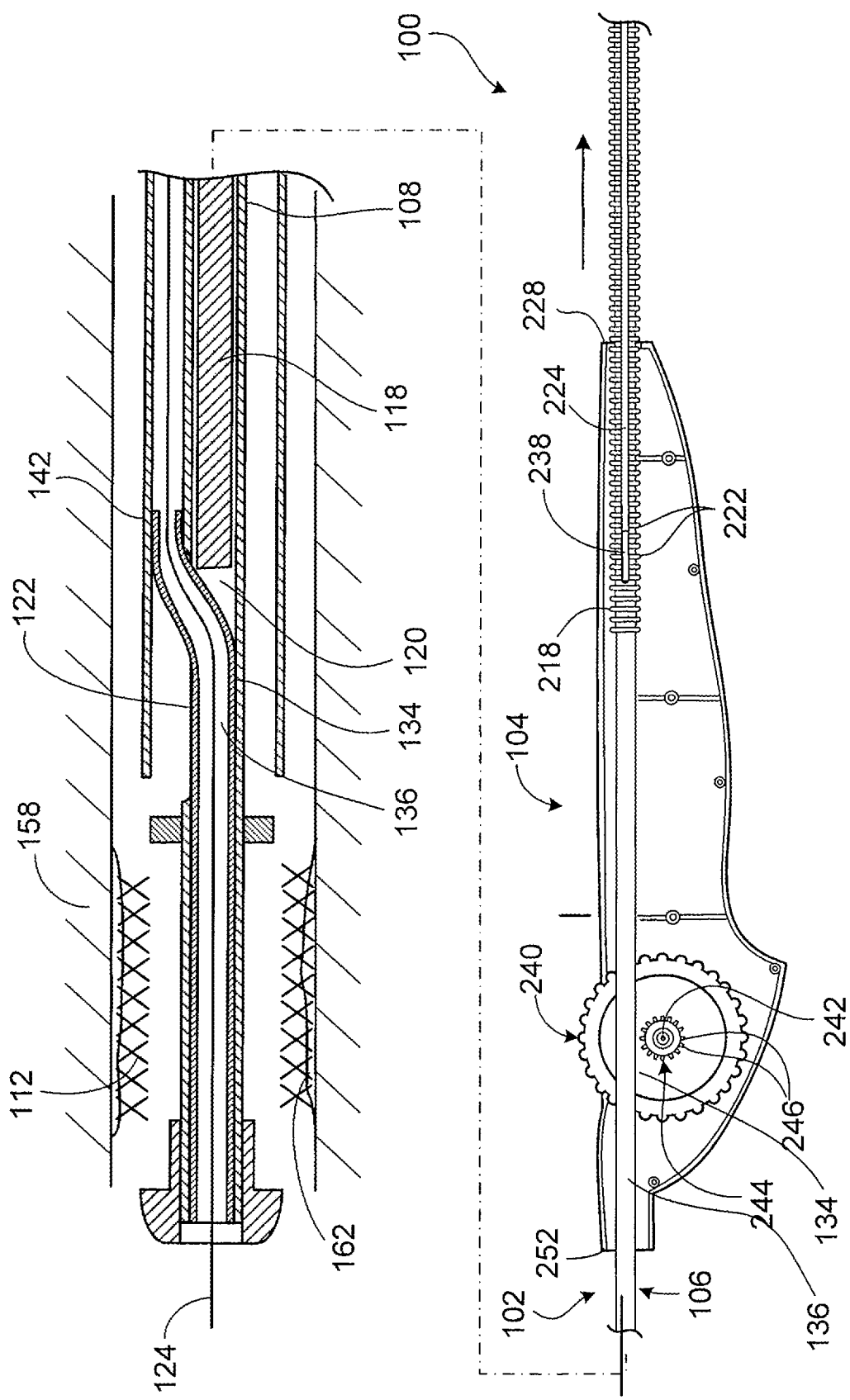

Referring to FIG. 7D, the user subsequently pulls proximally on pull grip 226 until the stent is fully deployed. For example, the user can pull proximally on pull grip 226 until the distal end of slot 224 abuts rib portion 238 of connector 234, preventing further retraction of tubular rack 218, support member 118, and distal and proximal outer sheaths 142, 143. In this fully retracted position, the entire length of tubular rack 218 is proximal to distal end 252 of handle assembly, and proximal portion of proximal outer sheath 143 resides within the cavity formed by housing 232 of handle assembly 104. Pull grip 226 generally permits the user to retract tubular rack 218, support member 118, and distal and proximal outer sheaths 142, 143 more rapidly than rotatable knob. In addition, pull grip 226 permits the user to retract distal and proximal outer sheaths 142, 143 even when the portion of tubular rack 218 that includes teeth 222 thereon has been retracted proximally beyond rotatable knob 240, rendering rotatable knob 240 incapable of retracting distal and proximal outer sheaths 142, 143 and support member 118 when rotated. As distal outer sheath 142 is retracted past the proximal end of stent 112, the full length of stent 112 is allowed to self-expand to a larger diameter and contact the blood vessel wall.

After deploying stent 112, system 100 and guide wire 124 are withdrawn from blood vessel 158, leaving stent 112 in blood vessel 158.

Due to the rapid exchange configuration of system 100, system 100 can be quickly exchanged with another system (e.g., a system of a different size or a different type of system) during use. To exchange systems, the user pulls handle assembly 104 proximally to move catheter assembly 102 proximally over guide wire 124. At the same time, the user holds the proximal end portion of guide wire 124 outside of the patient's body to help ensure that guide wire 124 remains in a substantially axially fixed position within the blood vessel. The user continues to retract catheter assembly 102 until the proximal end of guide wire 124 has passed distally beyond the distal end catheter assembly 102 (e.g., distally beyond the distal end of sleeve 134 and the tip of catheter assembly 102). At this point, the user can backload a new system over guide wire 124 and navigate the new system to a desired region of treatment within the blood vessel.

While certain embodiments have been described, other embodiments are possible.

As an example, while inner tubular member 108 has been described as being formed of stainless steel, it can be formed of any of various materials that allow it to be deflected and articulated, e.g., to traverse a tortuous body vessel. For example, as an alternative to or in addition to stainless steel, inner tubular member 108 can be formed of one or more other metals and/or alloys, such as Nitinol. Alternatively or additionally, inner tubular member 108 can include one or more polymeric materials, such as polyetheretherketone (PEEK) polymers, nylon, polyimides, and high durometer polyether block amides (e.g., PEBAX® 70D, PEBAX® 72D).

As another example, while system 100 has been described as including sleeve 134 disposed within a distal portion of lumen 120 of inner tubular member 108, certain embodiments include no such sleeve.

Figure 8:
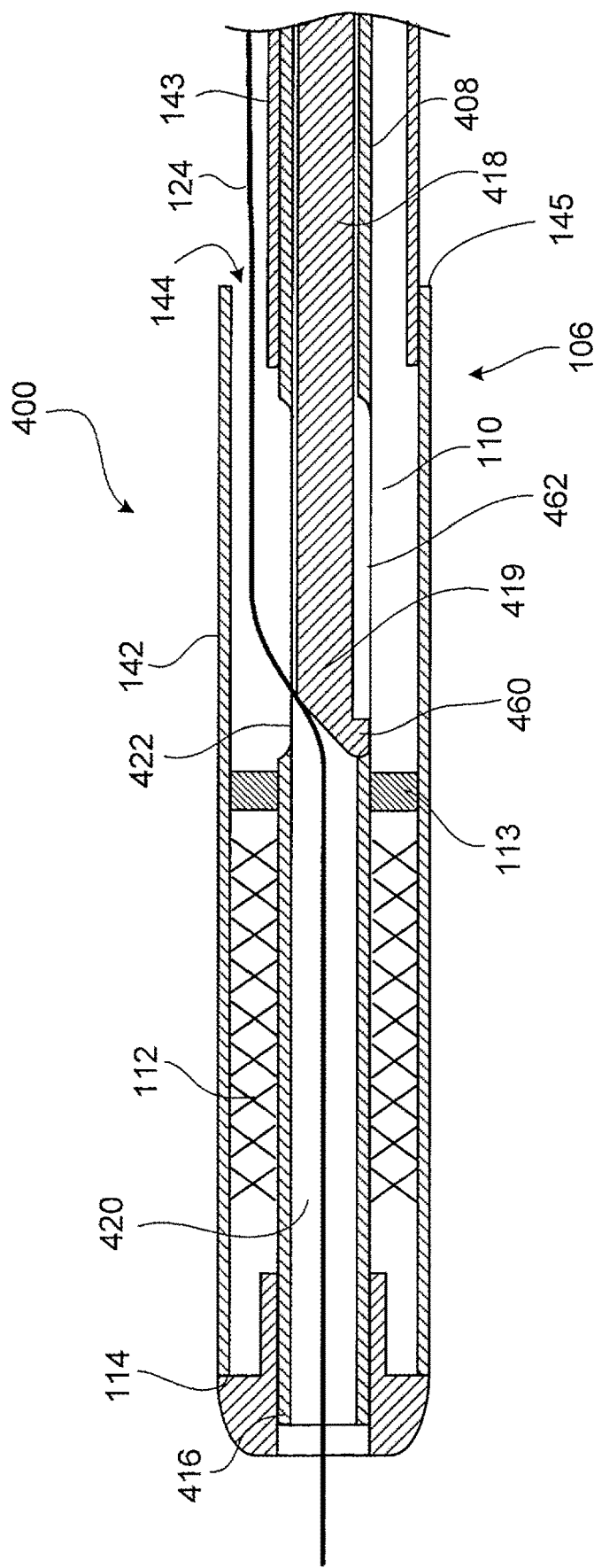
FIG. 8 is a cross-sectional view of a catheter assembly of a self-expanding stent delivery system including a support member with a distal ramped portion.

In some embodiments, the distal end of the support member is shaped to direct a guide wire toward port 144 of outer tubular assembly 106. For example, as shown in FIG. 8, the distal end of a support member 418 forms a ramped portion 419. In operation, the distal end portion of inner tubular member 408 is backloaded over the proximal end of guide wire 124. The catheter assembly is moved distally relative to guide wire 124 such that the proximal end of guide wire 124 moves within an inner lumen 420 of an inner tubular member 408, toward ramped portion 419 of support member 418. As the catheter assembly continues to move distally relative to guide wire 124, ramped portion 419 of support member 418 directs the proximal end of guide wire 124 out of inner lumen 420 through an elongate slot 422 formed in the side wall of inner tubular member 408. As the catheter assembly moves still further in the distal direction relative to guide wire 124, the proximal end of guide wire 124 exits the catheter assembly via port 144.

Still referring to FIG. 8, support member 418 includes a radial projection 460 configured to be received in a channel 462 formed in the side wall of inner tubular member 408. Radial projection 460 and channel 462 cooperate to limit rotation of support member 418 relative to inner tubular member 408. This arrangement helps to ensure proper orientation of support member 418 to allow guide wire 124 to be directed toward port 144. Moreover, this arrangement helps to ensure that this proper orientation of support member 418 is maintained while support member 418 is being retracted relative to inner tubular member 408.

As another example, while projection 460 in the system described above extends radially from the support member 418 and channel 462 is formed in the side wall of inner tubular member 408, other arrangements are possible. For example, in certain embodiments, the locations of the projection and channel are reversed such that the projection extends from the inner tubular member and the channel is formed in the support member.

Figure 9:
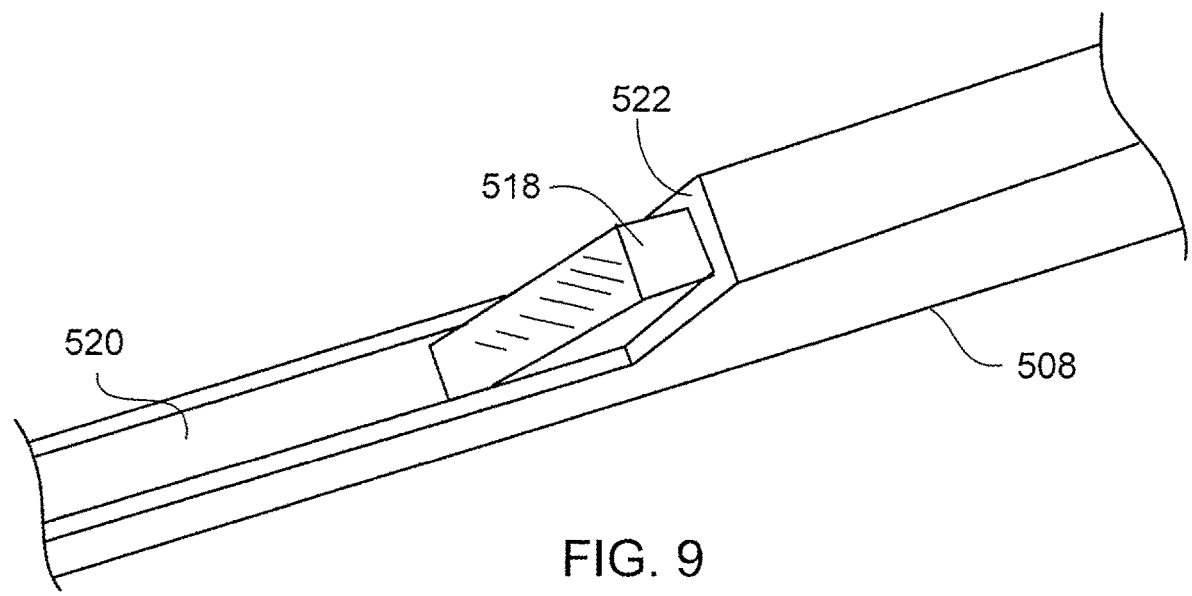
FIG. 9 is a perspective view of an inner tubular member having a lumen with a rectangular cross-section and a support member having a rectangular cross-section disposed in the lumen.

As still another example, while the support members and inner lumens of the above-described systems have circular cross-sectional areas, in some embodiments, at least a portion of the support member includes a non-circular cross-section and at least a portion of a lumen of the inner tubular member has a non-circular cross-section. For example, as shown in FIG. 9, a support member 518 and an inner lumen 520 of an inner tubular member 508 each have a rectangular (e.g., square) cross-section such that support member 518 is inhibited from rotating relative to inner tubular member 508. As an alternative to or in addition to rectangular cross-sections, any of various other cross-sections that can inhibit rotation of the support member relative to the inner tubular member can be used.

As another example, other embodiments for inhibiting rotation of the support member relative to the inner tubular member are possible. For example, the inner tubular member can include a lip extending into the inner lumen. The lip can be arranged to engage a ramped portion of the support member to inhibit further distal motion of the support member. The lip can be further arranged to limit rotational movement of the support member when the ramped portion of the support member is substantially engaged with the lip of the inner tubular member.

As yet another example, while the embodiments described above are configured to inhibit rotation of the support member relative to the inner tubular member, in certain embodiments, the support member is allowed to freely rotate relative to the inner tubular member.

As another example, while the inner tubular members of the systems above have been described as including an elongate slot defined by the sidewall of the inner tubular member, other types of openings can be formed in the sidewall of the inner tubular member to allow a guide wire to pass therethrough. For example, the sidewall of the inner tubular member can include a circular aperture, an elliptical aperture, etc.

As still another example, while the inner tubular members of the systems above have been described without a polymer coating, the inner member can include a polymer coating (e.g., to prevent sharp edges from apertures 130, 132 from causing damage to catheter assembly 102). For example, the inner tubular member can include a polymer coating over its entire length. As another example, the inner tubular member can include a polymer coating over a portion of the inner tubular member (e.g., in the region of apertures 130, 132). The polymer coating can include high durometer polyether block amides (e.g., PEBAX® 70D, PEBAX®72D), heat shrunk polyethylene terephthalate (PET), nylon, polyimides, a polytetra-fluroethylene (PTFE) sleeve, etc.

As another example, while first and second pattern of apertures 130, 132 in inner tubular member 108 have been described as including an interrupted spiral pattern and an uninterrupted spiral pattern, respectively, other arrangements can be used. For example, first and second apertures 130, 132 can each include an interrupted spiral pattern or can each include an interrupted spiral pattern. As another example, one or both of first and second apertures 130, 132 can include a combination of an interrupted and uninterrupted spiral pattern. As a further example, first and second apertures 130, 132 can include vertical slots extending substantially perpendicular to the longitudinal axis of inner tubular member 108. The vertical slots defining apertures 130 along first portion 126 of inner tubular member 108 can be substantially spaced apart to allow first portion 126 to allow some flexibility while enhancing overall pushability of the inner tubular member 108. The vertical slots defining apertures 132 along second portion 128 of inner tubular member 108 can be spaced close together (e.g., a minimum distance required to maintain structural strength of inner tubular member 108 along second portion 128) to allow second portion 128 to traverse tortuous regions of body vessels during use.

As still another example, in certain embodiments, distal outer sheath 142 includes a multi-layer construction to facilitate containing stent 112 in a compressed state prior to deployment. In certain embodiments, for example, distal outer sheath 142 includes an inner layer formed of PTFE, a middle layer formed of a stainless steel mesh, and an outer layer formed of nylon 12 and/or polyether block amide (e.g., PEBAX). Any of various techniques can be used to attach tubular rack to outer sheath. For example, tubular rack and outer sheath can be adhesively bonded, thermally bonded, welded, etc.

Figure 10:
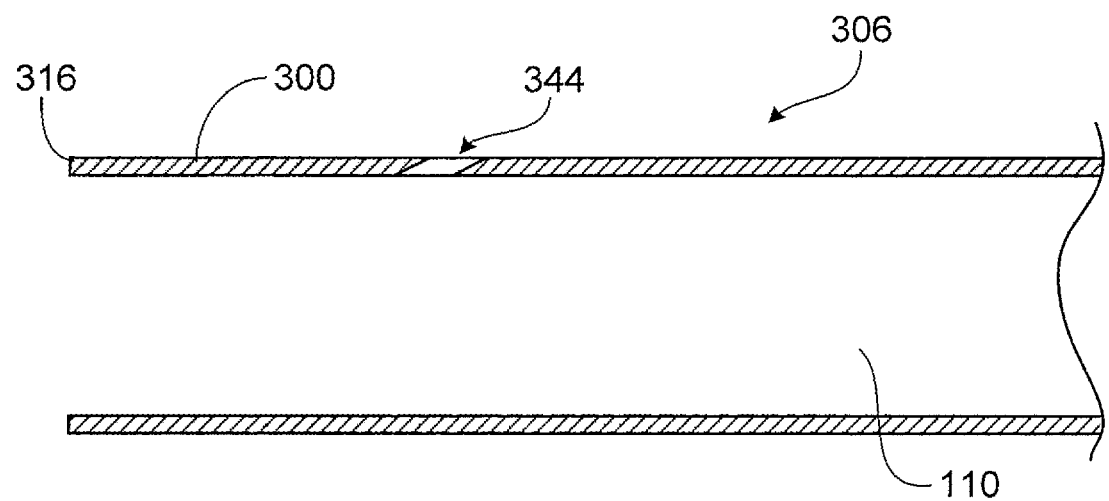
FIG. 10 is a cross-sectional view of a unitary outer sheath that has a guide wire exit port extending through its side wall.

As yet another example, while outer tubular assembly 106 has been described as including distal and proximal outer sheaths 142, 143, other embodiments are possible. For example, referring to FIG. 10, the outer tubular assembly can include a single, continuous outer sheath 300. A port 344 extends through the sidewall of continuous outer sheath 300, near distal end 316, to allow a guide wire to extend through the continuous outer sheath. Port 344 can extend at an acute angle (e.g., a 45 degree angle) relative to the longitudinal axis of outer sheath 300 to reduce stress imparted on a guide wire by continuous outer sheath 300 as the guide wire exits port 344 and extends substantially parallel to the longitudinal axis of the outer sheath 300. Such an angled arrangement can, for example, reduce friction between the guide wire and outer sheath 300 as outer sheath 300 is retracted relative to the guide wire. Additionally or alternatively, the port extending through the side wall of outer sheath 300 can extend at any of various other angles. In some embodiments, for example, the port extends substantially perpendicular to the longitudinal axis of outer sheath 300.

Figure 11:
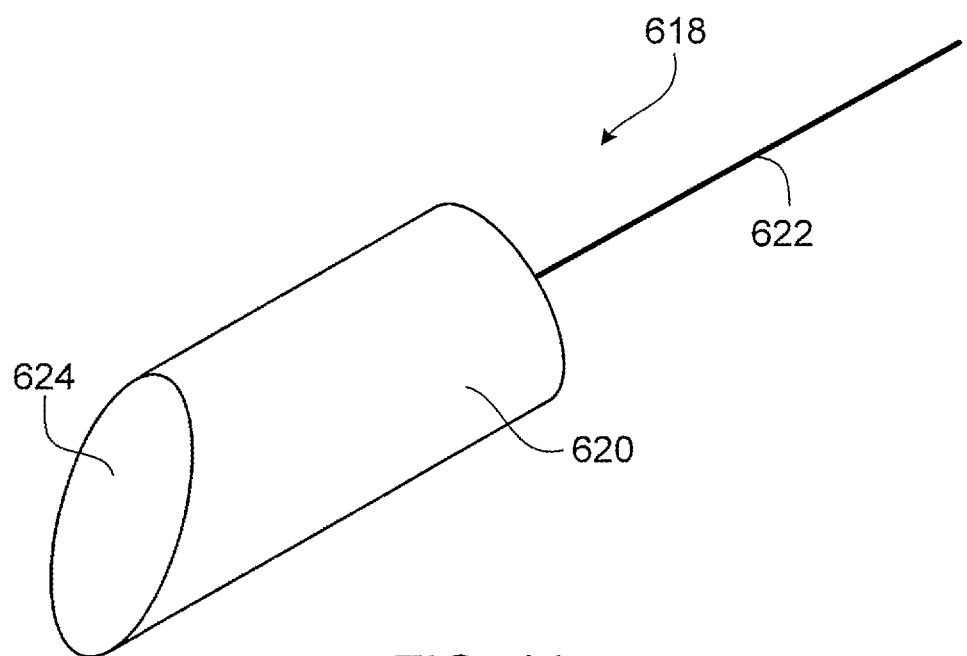
FIG. 11 is a perspective view of a support member that includes a support portion attached to a pull wire.

As still another example, while support member has been described as a solid wire or mandrel, other configurations can be used. For example, as shown in FIG. 11, a support member 618 includes a support portion 620 attached to a pull wire 622. This and other similar embodiments reduce the amount of material required to form the support member and help to localize added rigidity to the region of the inner tubular member in which the support portion is located. During use, support portion 620 can be positioned adjacent an elongate slot in an inner tubular member to prevent kinking, prolapsing, or otherwise deforming along the elongate slot of the inner tubular member. Pull wire 622 can be used to move support portion 620 in the distal direction as the stent is deployed. For example, pull wire 622 can be attached to a tubular rack in a manner similar to that in which support member 118 is attached to tubular rack 218.

As another example, while stent delivery system 100 has been described as including a support member, the stent delivery system 100 can be configured without a support member. In some embodiments, the portion of the inner tubular member proximal to the aperture is solid.

As a further example, while the stent deployment methods described above include retracting tubular rack 218, support member 118, and distal and proximal outer sheaths 142, 143 by rotating rotatable knob 240 and then pulling proximally on pull grip 226, other techniques can be used. In certain embodiments, for example, tubular rack 218, support member 118, and distal and proximal outer sheaths 142, 143 are retracted by pulling proximally on pull grip 226 only. Alternatively, tubular rack 218, support member 118, and distal and proximal outer sheaths 142, 143 can be retracted by rotating rotatable knob 240 only. In certain embodiments, tubular rack 218, support member 118, and distal and proximal outer sheaths 142, 143 are retracted for an initial distance by pulling proximally on pull grip 226 and then retracted the remaining distance by rotating rotatable knob 240.

As an additional example, while the systems above have been described as being used deliver and deploy self-expanding stents, in certain embodiments, the system can be used to deliver and deploy other types of implantable medical endoprostheses, such as stent-grafts, and filters (e.g., arterial and venous filters).

As another example, while the systems above have been described as being used in various different types of blood vessels, the systems can alternatively or additionally be used in any of various other types of body vessels. Other embodiments are in the claims.

What is claimed is:

1. A system, comprising:
   an inner member having a holding region;
   wherein the inner member has an elongate slot formed therein;
   an expandable implant disposed along the holding region;
   wherein the expandable implant has a first length, wherein the elongate slot has a second length, and wherein the second length is greater than or equal to the first length;
   a deployment sheath slidably disposed about the inner member;
   a rack coupled to the deployment sheath;
   a handle coupled to the rack;
   wherein the rack extends within the handle;
   wherein a distal portion of the rack is designed to extend distally of the handle; and
   wherein a proximal portion of the rack is designed to extend proximally of the handle.

2. The system of claim 1, wherein the handle includes an actuation member designed to engage the rack and designed to axially shift the deployment sheath relative to the inner member.

3. The system of claim 1, further comprising a pull grip coupled to the proximal portion of the rack.

4. The system of claim 1, wherein the rack includes a sidewall having a longitudinal slit.

5. The system of claim 1, wherein the inner member includes a cut portion.

6. The system of claim 1, further comprising a support member disposed within the deployment sheath.

7. A delivery system, comprising:
   an inner member having a holding region;
   an expandable implant disposed along the holding region;
   a deployment sheath slidably disposed about the inner member, the deployment sheath including a distal region disposed adjacent to the holding region, a proximal region disposed proximally of the holding region, and a rack region;
   a handle coupled to the deployment sheath;
   wherein the distal region of the deployment sheath has a first outer diameter, wherein the proximal region of the deployment sheath has a second outer diameter, and wherein the first outer diameter is different from the second outer diameter; and
   wherein the rack region is designed to extend within the handle, proximally of the handle, and distally of the handle.

8. The delivery system of claim 7, wherein the first outer diameter is greater than the second outer diameter.

9. The delivery system of claim 7, wherein the inner member includes an elongate slot.

10. The delivery system of claim 9, wherein the expandable implant has a first length, wherein the elongate slot has a second length, and wherein the second length is greater than or equal to the first length.

11. The delivery system of claim 9, wherein a sleeve is disposed adjacent to the elongate slot.

12. The delivery system of claim 11, wherein a port is defined at a proximal end of the sleeve.

13. The delivery system of claim 11, further comprising a support member disposed within the proximal region of the deployment sheath.

14. The delivery system of claim 13, wherein the support member has a distal end positioned adjacent to the sleeve.

15. The delivery system of claim 13, wherein the support member is free of a lumen.

16. The delivery system of claim 7, further comprising a pull grip coupled to a proximal end of the rack region.

17. A stent delivery system, comprising:
   an inner member having a stent holding region;
   a slot formed in the inner member;
   a sleeve coupled to the inner member adjacent to the slot;
   a stent disposed along the stent holding region;
   wherein the stent has a first length, wherein the slot has a second length, and wherein the second length is greater than or equal to the first length;
   a deployment sheath slidably disposed about the inner member, the deployment sheath including a distal region disposed adjacent to the stent holding region, a proximal region disposed proximally of the stent holding region, and a rack region;
   a support member disposed within the deployment sheath, the support member having a distal end positioned adjacent to the sleeve;
   a handle coupled to the deployment sheath; and
   wherein the rack region has a distal end disposed distal of the handle, a central portion disposed within the handle, and a proximal end disposed proximal of the handle.

* * * * *